United States Patent
Zimmermann et al.

[11] Patent Number: 5,849,176
[45] Date of Patent: Dec. 15, 1998

[54] PROCESS FOR PRODUCING THERMALLY CRACKED PRODUCTS FROM HYDROCARBONS

[75] Inventors: Gerhard Zimmermann; Wolfgang Zychlinski, both of Leipzig, Germany

[73] Assignees: Mannesmann Aktiengesellschaft, Düsseldorf, Germany; K.T.I. Group B.V., AB Zoetermeer, Netherlands

[21] Appl. No.: 696,934
[22] PCT Filed: Feb. 16, 1995
[86] PCT No.: PCT/DE95/00233
§ 371 Date: Aug. 21, 1996
§ 102(e) Date: Aug. 21, 1996
[87] PCT Pub. No.: WO95/22587
PCT Pub. Date: Aug. 24, 1995

[30] Foreign Application Priority Data

Feb. 21, 1994 [DE] Germany .................. 44 05 883.7

[51] Int. Cl.⁶ ............................................. C10G 9/16
[52] U.S. Cl. ................... 208/48 R; 208/48 AA; 208/130; 208/131; 585/648; 585/650; 585/950
[58] Field of Search .................. 585/648, 650, 585/950; 208/48 R, 48 AA, 130, 131

[56] References Cited

U.S. PATENT DOCUMENTS

| | | | |
|---|---|---|---|
| 4,024,049 | 5/1977 | Shell et al. | 208/48 AA |
| 4,692,234 | 9/1987 | Porter et al. | 208/48 AA |
| 4,756,819 | 7/1988 | Bousquet et al. | 208/48 AA |

Primary Examiner—Bekir L. Yildirim
Attorney, Agent, or Firm—Cohen, Pontani, Lieberman & Pavane

[57] ABSTRACT

The invention relates to the protection of tubular reactors or heat exchangers against coke formation in plants for converting hydrocarbons and other organic compounds at high temperatures in the gaseous phase. The problem in such plants is that the usual steam/air cleaning processes for removing coke deposits lead to an increase in the catalytic activity of the material surfaces, which in turn shortens the service life of the plants. The object of the invention is to substantially reduce coking and to maintain the long-term passivity of steels for long operational periods. According to the invention, the process for producing thermally cracked products from hydrocarbons while simultaneously reducing the coke deposits on heat exchange surfaces is characterized by the fact that 20 to 1000 ppm of an additive composition containing organically bound silicon and organically bound sulphur is added to the feed to be cracked and the mixture is brought into contact with the heat exchange surfaces at temperatures from 400° to 1000° C.

13 Claims, 7 Drawing Sheets

PROCESS FOR PRODUCING THERMALLY CRACKED PRODUCTS FROM HYDROCARBONS

FIELD OF THE INVENTION

The invention relates to a process for producing thermally cracked products from hydrocarbons and simultaneously reducing the coking on heat exchange surfaces in reactors for the thermal cracking of organic compounds.

BACKGROUND OF THE INVENTION

To produce ethylene and other alkenes, hydrocarbons or hydrocarbon mixtures are thermally cracked in externally-heated reactors of metal materials. The cracking furnaces preferably consist of high-temperature-resistant tubes containing chrome and nickel.

The effectiveness of tubular reactors depends heavily on whether coke deposits that interfere with heat transfer form on the inner surfaces of the reactor tubes during operation. This generally happens in the reactors in use today. After operational periods of between one week and three months, the deposits formed on the reactor interiors that come into contact with the hydrocarbons become so extensive that the resulting decline in performance necessitates shut-downs and expensive cleaning procedures. The coke deposits are usually removed by means of gassing with a mixture of hot steam and air, which uncovers the metal surfaces and permits the desired heat flow to again be achieved. However, in spite of the thorough removal of deposited coke, new deposits can form and necessitate renewed shut-down and decoking after relatively short periods of operation. Because the oxidative decoking procedures that are used lead to high-temperature corrosion of the tubes, which in turn creates reaction products that catalyze coke formation, the deposit of coke accelerates after each decoking. For this reason, the operational periods between decokings grow shorter as the number of decoking cycles increases. This is undesirable from the technical as well as the economic point of view, because it interferes with steady long-term operation, reduces plant efficiency and requires more frequent cleaning expenditures. Attempts have therefore been made for years to find solutions that counteract the rapid formation of coke on the inner surfaces of tubular reactors. In some plants, a treatment with alkyl-ammonia sulfonates is used to achieve this object; however, this treatment does not result in reduced coke formation U.S. Pat. No. 4,105,540 describes the addition of small amounts of phosphoric and phosphorous acid esters, while U.S. Pat. No. 4,551,227 describes the addition of a combination of tin and phosphorous compounds; phosphorous and antimony or tin compounds; or antimony and phosphorous compounds as anti-foulants. U.S. Pat. No. 3,647,677 and U.S. Pat. No. 3,531,394 propose the use of elementary phosphorous and phosphorous compounds as anti-foulants in refinery plants and steam cracking plants, respectively. This also applies analogously to U.S. Pat. No. 4,835,332 (tri-phenyl-phosphine), U.S. Pat. No. 4,900,426 (tri-phenyl-phosphine-oxide) and U.S. Pat. No. 4,842,716, which describes the addition of a combination of a phosphorous anti-foulant and an inhibitor (imidazoline) that favors film formation. Finally, gaseous or vaporous sulphur-containing compounds, as described in the publication by Boene, K.: Oil Gas J. 81 (1983) 93, and nitrogen-containing compounds are described as additives with an anti-fouling effect. All of these additives evidently lead to a limited reduction in the coking tendency, but without inhibiting the carburization of the surface layers of the material, which must be understood as the start of an undesirable reaction cascade. Because catalytically active centers are created at the end of this process, the use of such anti-foulants addresses the symptoms, but not the causes, of coke formation.

It is known that the carburization of metal surfaces is inhibited by relatively high silicon contents in these surface layers, as described in the publication by Norton, J. F. and Barnes J.: Corrosion in Fuel Systems, The Electrochemical Soc., Pennington N.J. (1983) 277, whereby this inhibition evidently gradually declines under the conditions of thermal cracking by depletion of the silicon species.

It is also known that anti-foulants which consist of combinations of inorganic and/or organic Si compounds and Sn compounds and/or Sb compounds have a coke-inhibiting effect during the production of cracking products as described in European patent publication EP-A-0241020.

SUMMARY OF THE INVENTION

The object of the invention is therefore to suggest a solution with which the coke formation is substantially reduced and at the same time the long-term passivity of high-temperature steels with relatively high silicon contents in the surface layer is maintained over long operational periods.

According to the invention, the process for producing thermally cracked products from hydrocarbons while simultaneously reducing the coke deposits on the heat exchange surfaces consists in adding to the feed to be cracked, before the cracking temperature is reached, 20 to 1000 ppm of an additive composition that is selected from among:

(1) one or more volatile organic compounds containing silicon and sulphur;

(2) a mixture of volatile organic compounds containing silicon and volatile organic compounds containing sulphur;

(3) a mixture of volatile organic compounds containing silicon and sulphur and volatile organic compounds containing silicon and/or volatile organic compounds containing sulphur; or (4) in the case of feeds rich in sulphur, having greater that 100 ppm sulphur, in which the sulphur component becomes volatile under cracking conditions, only volatile organic compounds containing silicon, at a maximum, however, 300 ppm of the pure silicon-containing compound;

whereby in all cases the atomic ratio of silicon and sulphur is between 5:1 and 1:1; and whereby in all cases organic sulphur-containing silicon compounds in which the sulphur is bound to the silicon atom via an alkyl residue or an alkoxy residue are excluded, as are organic heavy metal compounds containing sulphur;

and the mixture is brought into contact with the heat exchange surfaces, which have temperatures in the range from 400° to 1000° C.

The temperature used is between 700° and 1000° C. when the heat exchange surface is the metal inner wall of a tubular reactor. The temperature is between 400° and 750° C. when the heat exchange surface is the metal surface of a heat exchanger, for example, which is connected downstream to the tubular reactor; in individual cases, the temperature at the input of the heat exchanger (impact plate) can also locally exceed 800° C., e.g./875° C.

The compound containing silicon and/or sulphur is preferably selected from the group that consists of tri-methyl-silyl-mercaptan, di-methyl-sulfide, tetra-methyl-silane and bis-tri-methyl-silyl-sulfide and their mixtures. However, other volatile compounds can also be used, insofar as the object of the present invention is achieved with their use.

When a feed especially rich in sulphur is used, it is possible, as applicable, to dispense with the volatile compound containing sulphur and add only the volatile compound rich in silicon, as long as an atomic ratio according to the invention in the range from 5:1 to 1:1 is attained and the sulphur component in the feed becomes volatile under cracking conditions. For example, this embodiment of the invention can be implemented when the feed contains greater than 100 ppm sulphur; in this case, however, a maximum of 300 ppm of the silicon-rich compound should be added.

The invention is based on the surprising discovery that when volatile organic compounds that contain either silicon and sulphur or a mixture of silicon and sulphur are added to pyrolysis feeds, the compounds evidently serve under pyrolysis conditions, first of all, to continually replenish the silicon level, which is depleted during thermal cracking, in the surface layer of the metal materials containing silicon, and thus to hold the coke formation ad hoc to a low level and, secondly, to significantly reduce coke formation on the heat exchange surfaces of tubular reactors made of relatively low-silicon steels.

Organic compounds containing only silicon display no inhibiting effect on coke formation, while compounds containing only sulphur are not able to counteract the surface carburization that is responsible for the formation of catalytically active centers.

In order to achieve both effects—but particularly the long-term passivity of the heat exchange surfaces of tubular reactors that come into contact with cracking products—the invention calls for treating the feed hydrocarbons to be thermally cracked, prior to the actual start of cracking reactions, with at least 20 ppm and preferably 50 to 400 ppm, especially 50 to 200 ppm, of a volatile organic compound containing silicon and sulphur or with a mixture of volatile silicon compounds and volatile sulphur compounds. Advantageously, this is done by establishing a solution of these compounds in a suitable hydrocarbon fraction and then continuously adding this solution in doses to the hydrocarbon fraction to be cracked. In this way, the low coking rates typical for the inner surfaces of cracking tubes of steels containing silicon can be maintained for long operational periods.

It has proved advantageous to treat the hydrocarbons to be thermally cracked, before the actual cracking temperature is reached, with an additive that consists either of a volatile compound containing silicon and sulphur in the atomic ratio 5:1 to 1:1 or of a mixture of a compound containing silicon and a compound containing sulphur in the same atomic ratio.

The cracked end product is preferably selected from the group that consists of alkenes, such as ethylene, propylene, butadiene and other lower olefines and diolefines.

The invention is described below in reference to several comparative examples and examples of embodiments according to the invention. FIGS. 1 to 7 show, in respect to pre-activated samples of chrome-nickel-steel and samples that display a reduced coking tendency due to special thermal pretreatment with compounds containing silicon and sulphur, the dependency of coke formation rates on test time during the pyrolysis of n-heptane in nitrogen and in steam as the dilutent when known coke formation inhibitors and inhibitors according to the invention are added.

DESCRIPTION OF THE PRESENTLY PREFERRED EMBODIMENTS

EXAMPLE 1

(Comparative Example)

In an electrically heated laboratory pyrolysis apparatus of quartz (vertically arranged laboratory tubular reactor ($d_i$=20 mm; $V_R$=13 ml)), in the interior of which there is a material sample connected to a microthermal scale via a thin platinum wire (cf. J. Anal. Appl. Pyrolysis 27 (1993) 45), n-heptane was subjected to pyrolysis under normal pressure in nitrogen or steam as the dilutent at temperatures between 700° and 800° C. and standing times (τ) of approximately 1 s. The n-heptane throughput was 14 ml/h; the dilutent throughput was 5 l/h. The weight ratio of ethylene to propylene in the cracked gas was 2.0 to 2.7 under the given conditions. The samples measured 30×7×1 mm.

The weight change in the sample resulting from coke that formed on its surface was measured continuously and the coke formation rate ($\mu$g/cm$^2$·min) in dependence on test time was determined. In order to reliably assess the effect of the coke formation inhibitors added in amounts from 10 to 250 ppm to the n-heptane prior to its entry into the pyrolysis apparatus, coke formation rates in the range from 50 to 300 $\mu$g/cm$^2$·min were set during the use of pure n-heptane. This made it necessary to increase the catalytic activity of the material surface through repeated coking and decoking by air (pre-activation of samples to achieve catalytic activity, as found in industrial plants only after repeated decoking).

Figure 1:
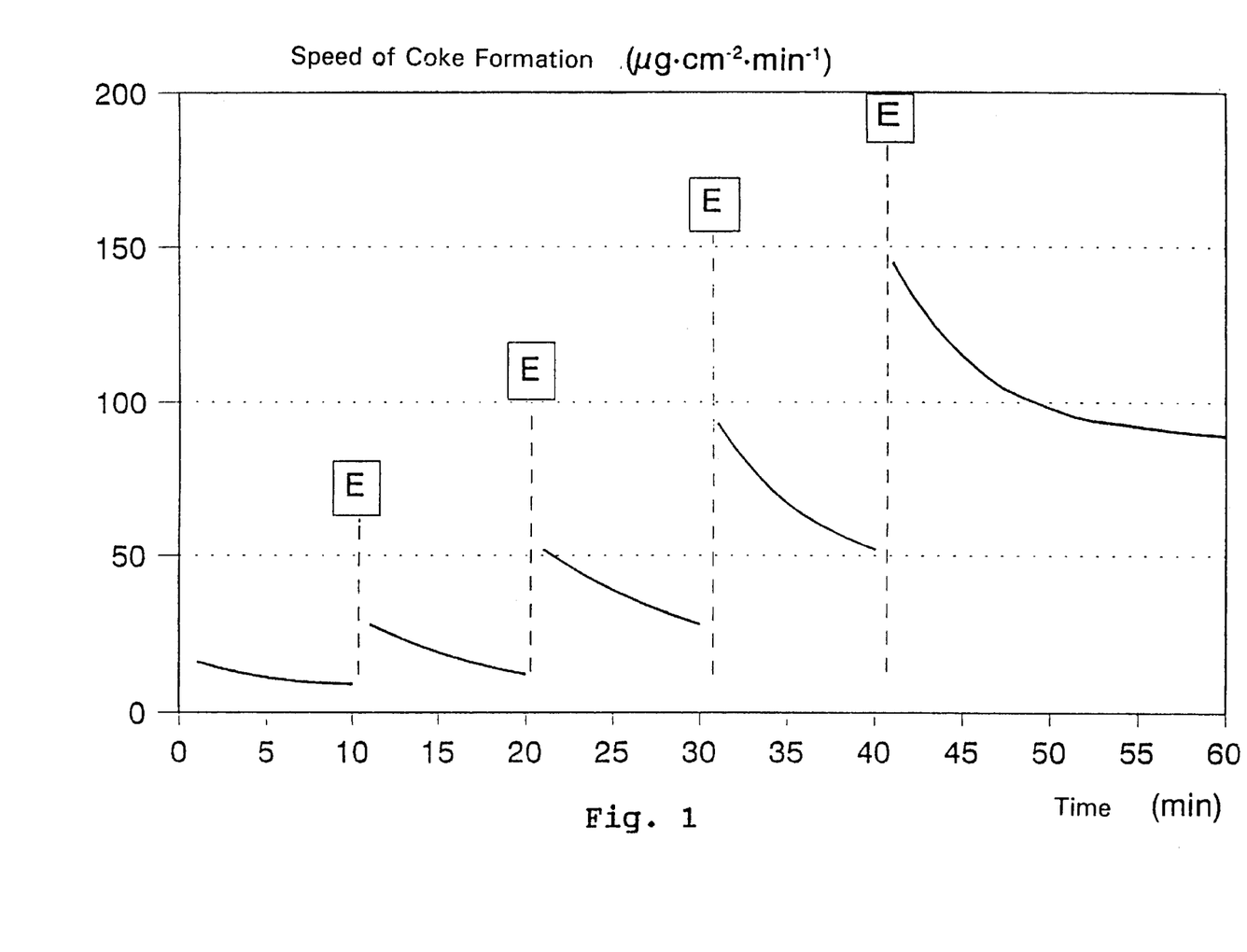
FIG. 1: On a pre-activated sample of chrome-nickel-steel (X8CrNiTi18.10): Dependence of the coke formation rate on the test time and number of decokings by air (E) during n-heptane pyrolysis in nitrogen ($T_R$=715° C., τ=1 s)

FIG. 1 shows a typical curve of the coke formation rate on the surface of a chrome-nickel-steel sample relative to test time during the pyrolysis of pure n-heptane in nitrogen at 715° C. for five consecutive coking-decoking cycles.

EXAMPLE 2

(Comparative Example)

Figure 2:
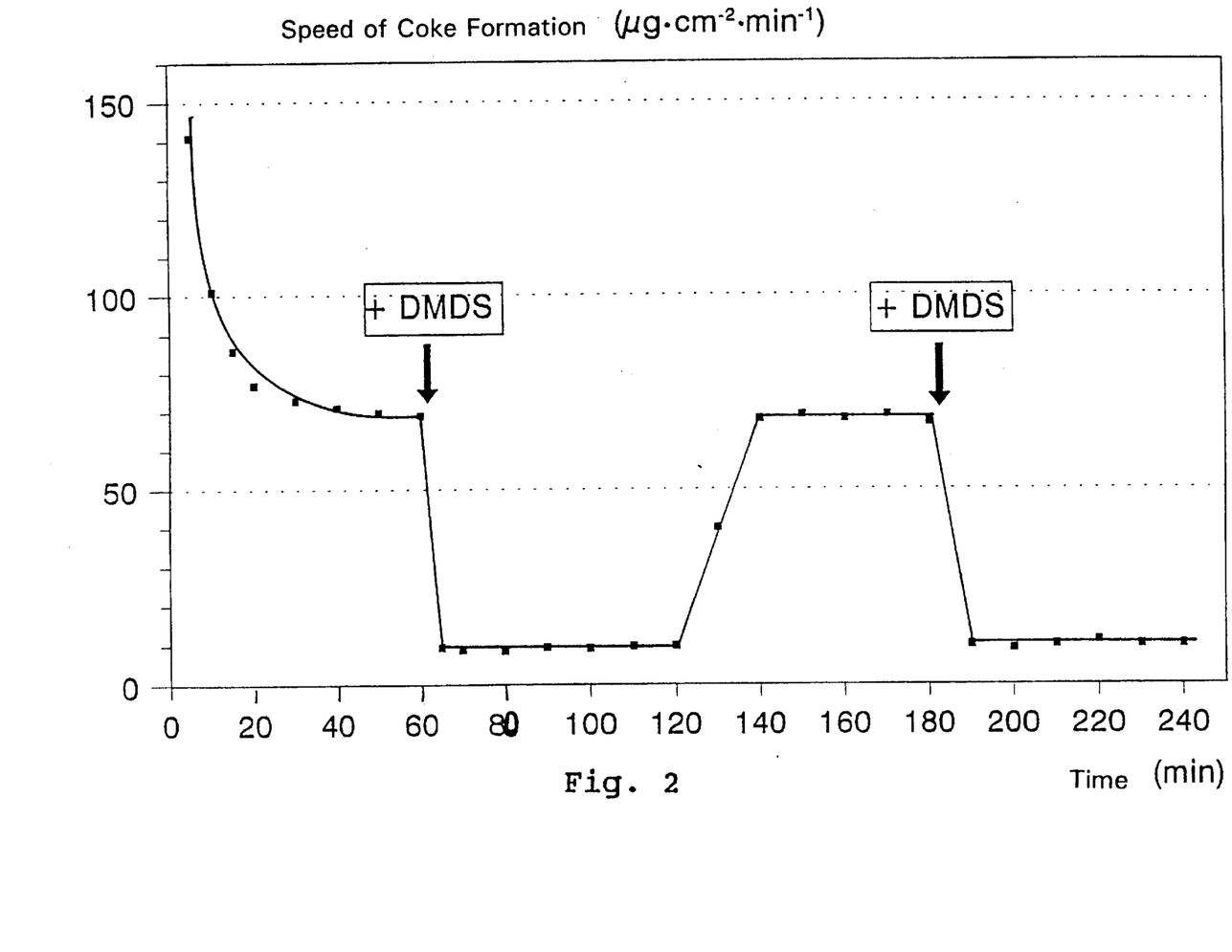
FIG. 2: On a pre-activated sample of chrome-nickel-steel (X8CrNiTi18.10): Dependence of the coke formation rate on the test time during n-heptane pyrolysis without and with the addition of 85 ppm di-methyl-di-sulfide (DMDS) ($T_R$=715° C., τ=1 s)

In the same apparatus as described in Example 1, first, pure n-heptane was subjected to pyrolysis in the presence of a pre-activated sample of chrome-nickel-steel (X8CrNiTi18.10) at 715° C. in the presence of nitrogen and the coke formation rate was tracked, After 60 minutes, the supply of pure n-heptane was then interrupted, and the feed was switched to a mixture in which 85 ppm di-methyl-disulfide (DMDS) was dissolved in n-heptane. As FIG. 2 shows, after the change in feed, there was a drastic reduction in the coke formation rate, which was nullified again after the feed was switched back to pure n-heptane.

EXAMPLE 3

(Comparative Example)

Figure 3:
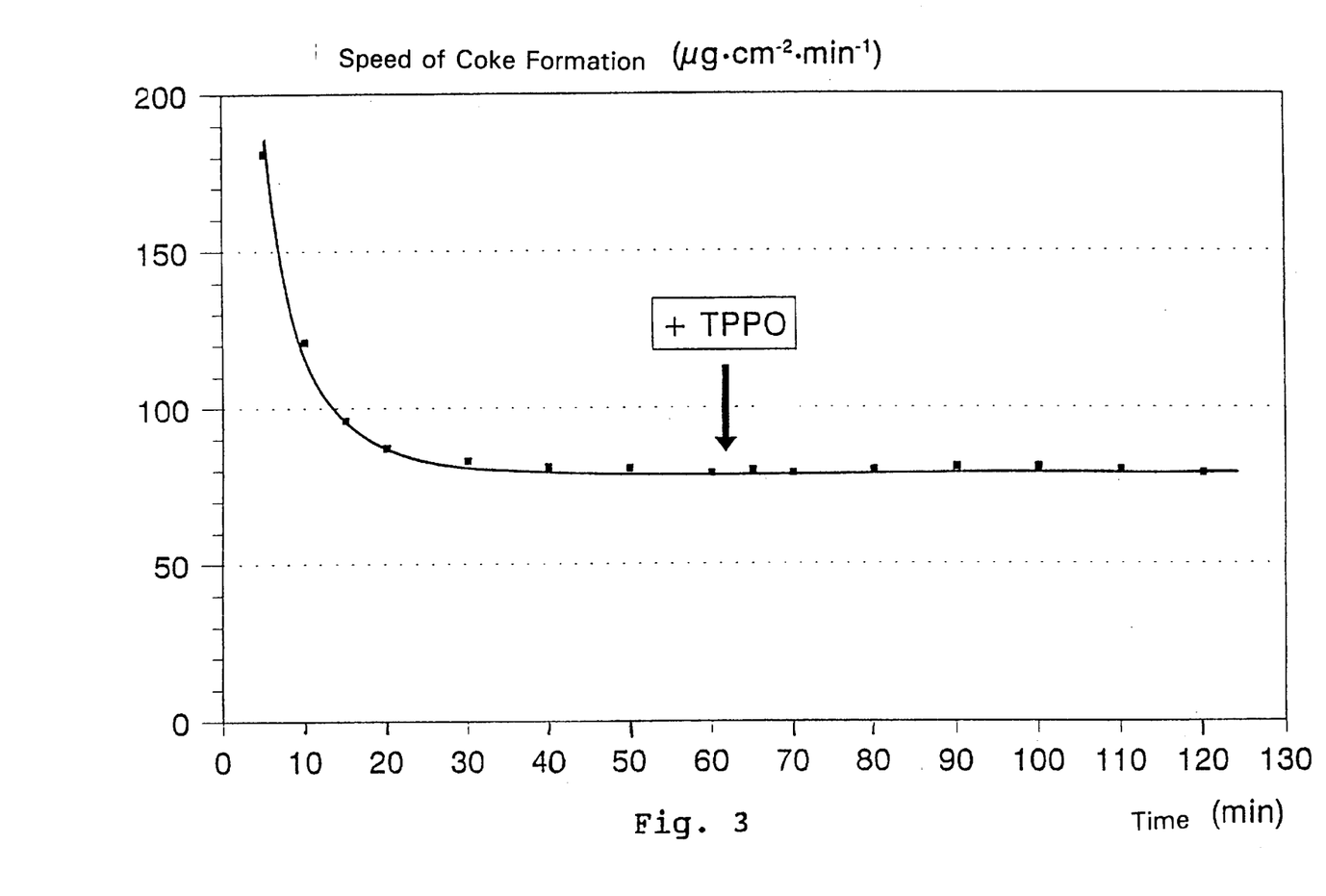
FIG. 3: On a pre-activated sample of chrome-nickel-steel (X8CrNiTi18.10): Dependence of the coke formation rate on the test time during pyrolysis of pure n-heptane and an n-heptane containing 1000 ppm tri-phenyl-phosphine-oxide (TPPO) ($T_R$715° C., τ=1 s)

In the same apparatus as described in Example 1 and under the conditions described in Example 2, the effect of tri phenyl-phosphine-oxide (TPPO) (see U.S. Pat. No. 4,900, 426 of Feb. 13, 1990) instead of dimethyl disulfide was investigated. The results are shown in FIG. 3. When the switch was subsequently made from pure n-heptane to a mixture of n-heptane treated with 1000 ppm tri-phenyl-phosphine-oxide, there was no significant influence on coke formation under the given test conditions.

EXAMPLE 4

(Comparative Example)

In the same apparatus as described in Example 1 and under the conditions described in Examples 2 and 3, the influence of tetra-methyl-silane (TMSi) on coke formation was investigated.

Figure 4:
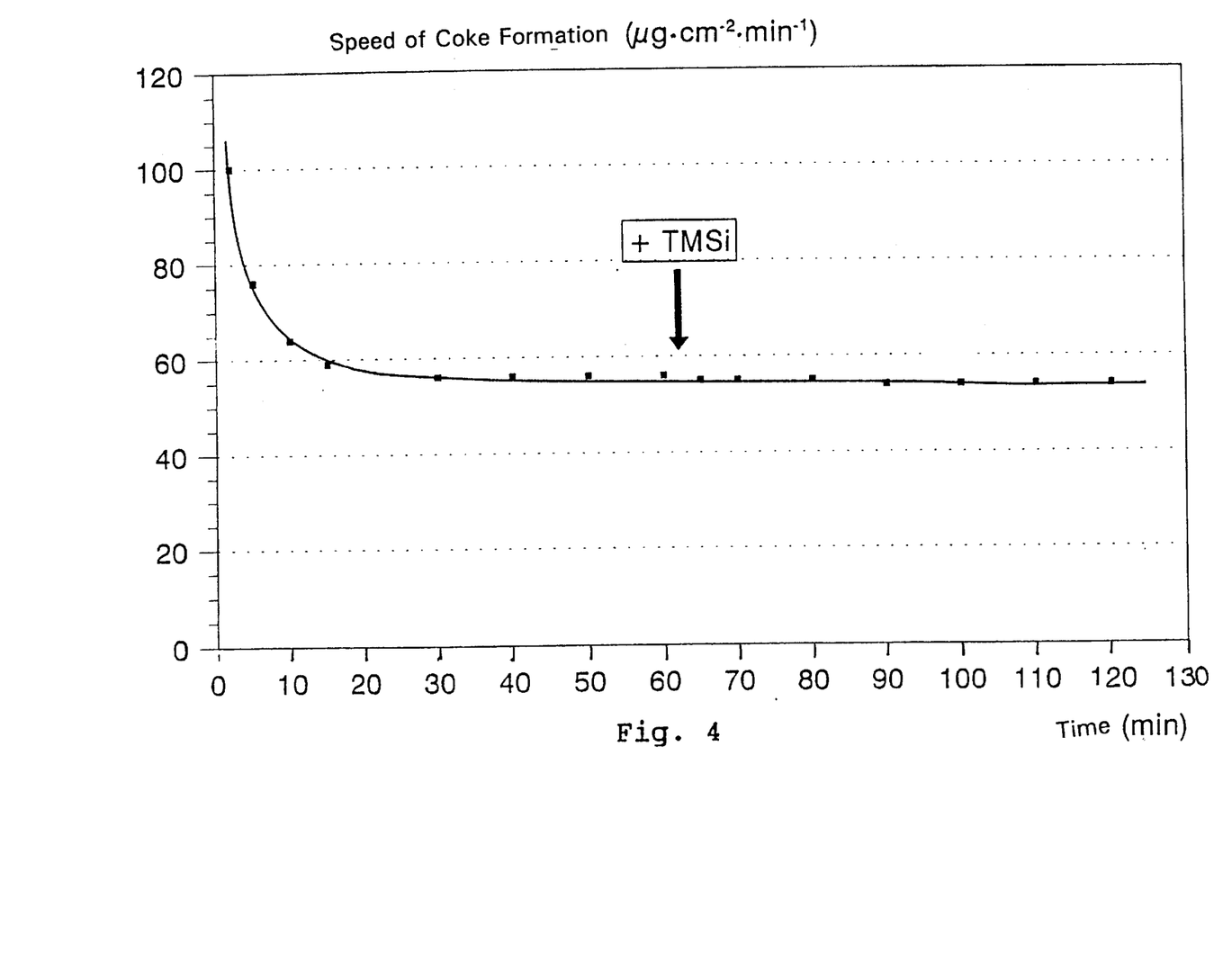
FIG. 4: On a pre-activated sample of chrome-nickel-steel (X8CrNiTi18.10): Dependence of the coke formation rate on the test time during pyrolysis of n-heptane without and with the addition of 100 ppm tetra-methyl-silane (TMSi) ($T_R$= 715° C., τ=1 s)

The results are shown in FIG. 4. When the switch was subsequently made from pure n-heptane to an n-heptane treated with 100 ppm tetra-methyl-silane, there was no significant drop in the coke formation rate.

EXAMPLE 5

(Comparative Example)

Figure 5:
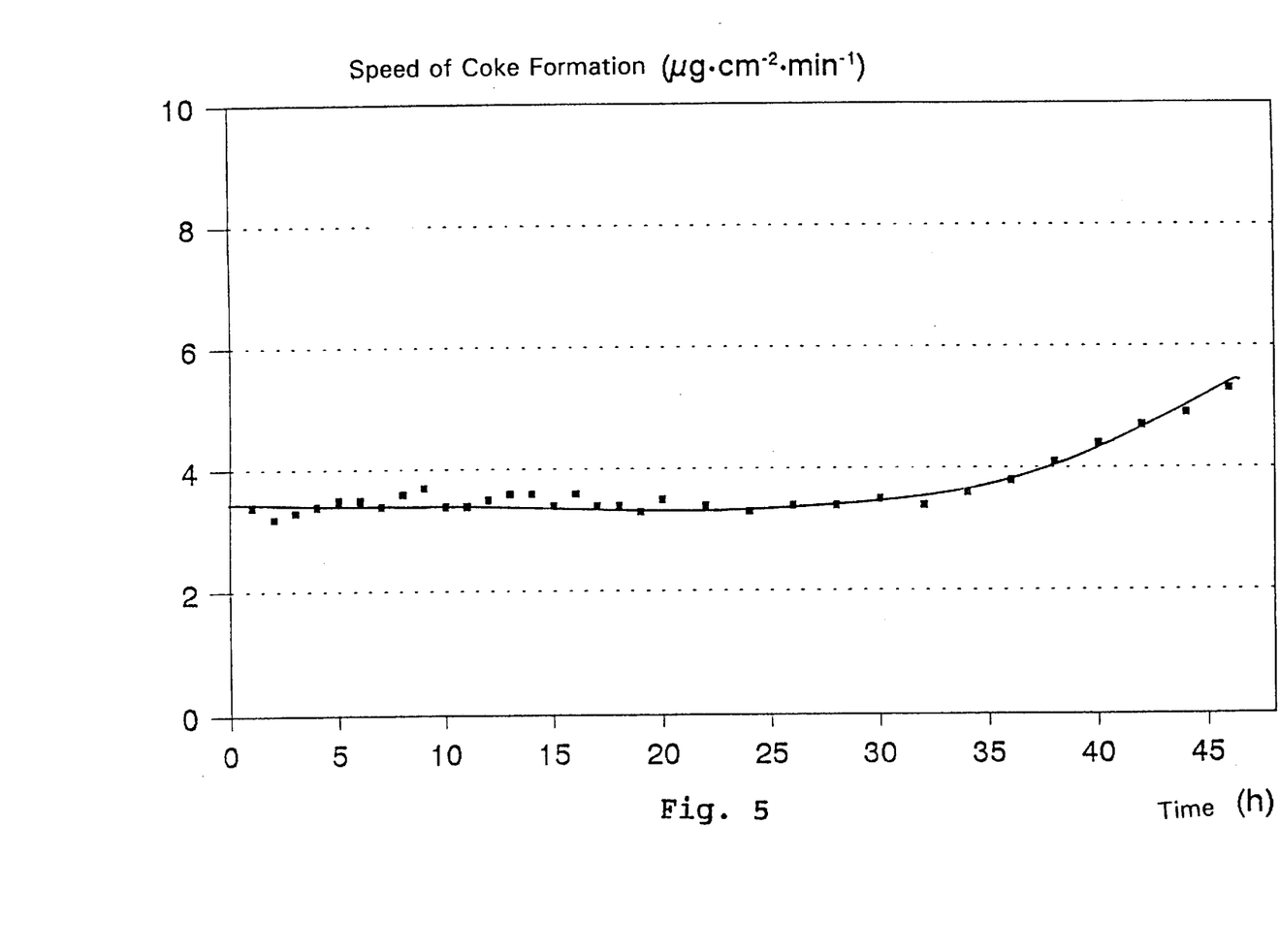
FIG. 5: On a sample of chrome-nickel steel (X8CrNiTi18.10) thermally pretreated at 880° C. with tri-methyl-silyl-methyl-mercaptan: Dependence of the coke formation rate on the test time during pyrolysis of pure n-heptane $T_R$=715° C., τ=1 s)

In the same apparatus as described in Example 1, a pre-activated sample of chrome-nickel-steel (X8CrNiTi18.10) was first thermally pretreated with 3 l of an equimolar mixture of hydrogen and methane containing 0.005 mol of tri-methyl-silyl-methyl-mercaptan for 60 minutes at 880° C. according to a process also registered by the present inventors. The apparatus was rinsed with nitrogen; after this, the coke formation rate during the pyrolysis of pure n-heptane in nitrogen as the dilutent ($n_{heptane}:n_{N2}=0.5$) for a test time of 45 hours was found. The results are shown in FIG. 5. FIG. 5 indicates that the low coke formation rates typical for thermal pre-treatments of this type rise after approximately 35 hours.

EXAMPLE 6

(Example According to the Invention)

In the same apparatus as described in Example 1 and under analogous external conditions based on Examples 2 to 4, the influence of tri-methyl-silyl-methyl-mercaptan on the coke formation rate on samples of chrome-nickel-steel (X8CrNiTi18.10) that were thermally pretreated with tri-methyl-silyl-methyl-mercaptan as in Example 5 was investigated in a long-term test.

Figure 6:
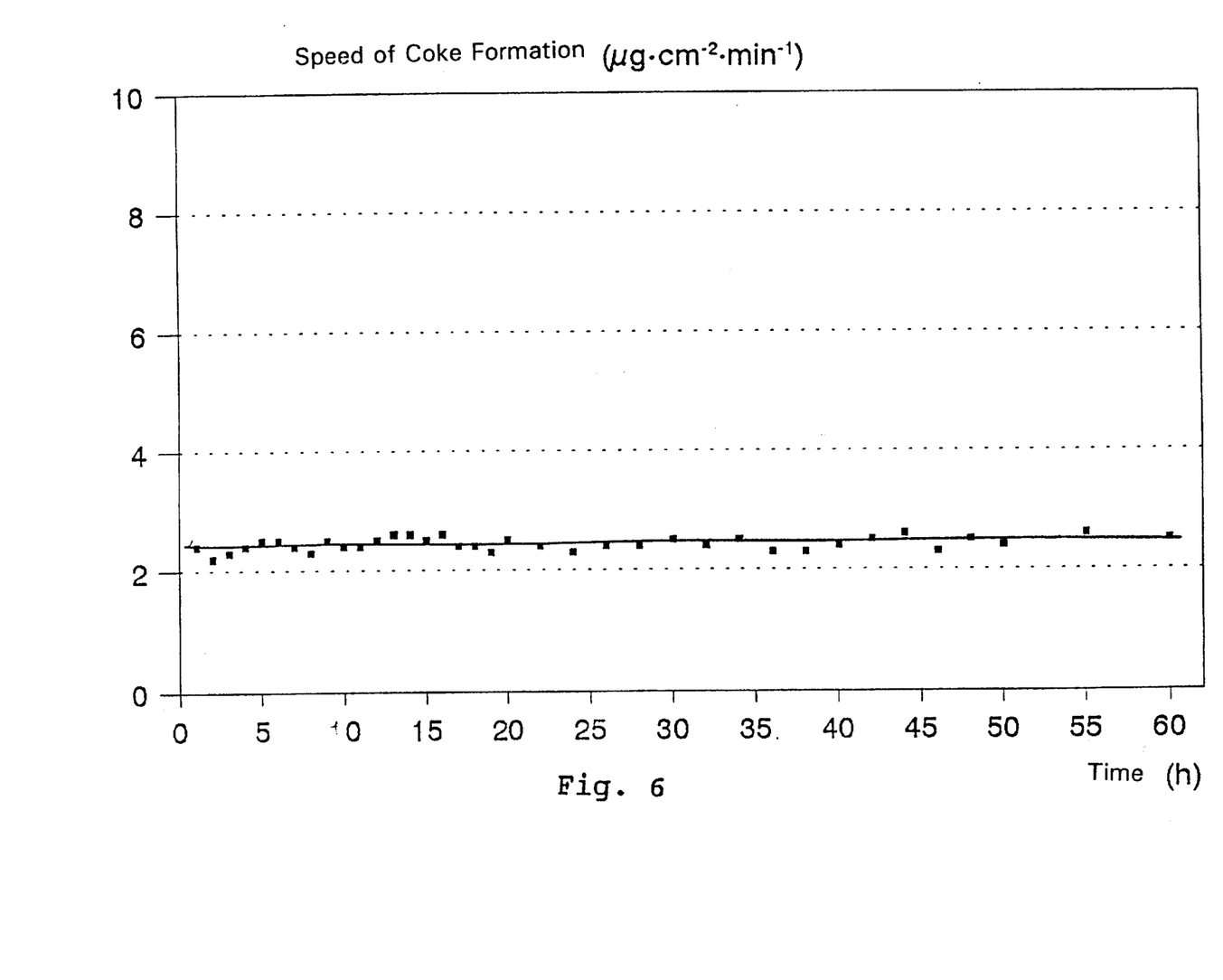
FIG. 6: On a sample of unused chrome-nickel-steel (X8CrNiTi18.10) thermally pretreated with tri-methyl-silyl-methyl-mercaptan at 880° C.: Dependence of the coke formation rate on the test time during n-heptane pyrolysis in the presence of 100 ppm tri-methyl-silyl-methyl-mercaptan as an additive.

The results are shown in FIG. 6. A comparison shows that the low coke formation rate on the sample thermally pretreated with tri-methyl-silyl-methyl-mercaptan as in Example 5 can be further reduced by adding 100 ppm of this compound to the n-heptane and, furthermore, that the increase in the coke formation rate that begins after approximately 35 test hours when no tri-methyl-silyl-methyl-mercaptan is added can be avoided by means of this continuous supplementary addition of tri-methyl-silyl-methyl-mercaptan as an additive to the pyrolysis feed.

EXAMPLE 7

(Example According to the Invention)

Figure 7:
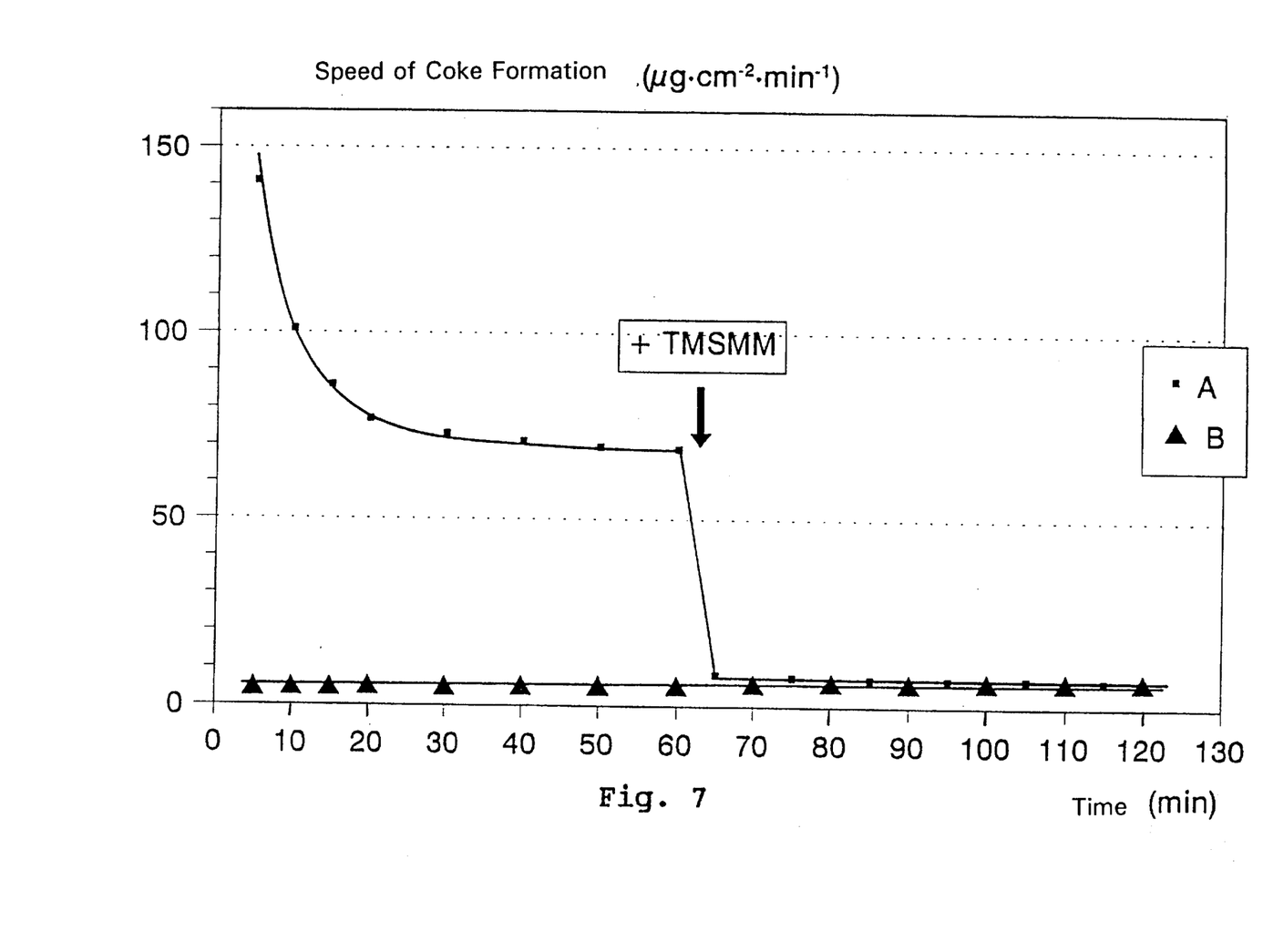
FIG. 7: On pre-activated samples of chrome-nickel-steel (X8CrNiTi18.10): Influence on the coke formation rate during pyrolysis of n-heptane in the absence (Curve A, first section) and presence (Curve B; Curve A, section second) of 100 ppm tri-methyl-silyl-methyl-mercaptan (TMSMM).

In the same apparatus as described in Example 1 and under external conditions analogous to those described in Examples 2 to 4, the influence of 100 ppm tri-methyl-silyl-ethyl-mercaptan (TMSMM) on the coke formation rate during n-heptane pyrolysis was investigated. First, the curve of the coke formation rate upon switchover from pure n-heptane to an n-heptane treated with 100 ppm tri-methyl-silyl-methyl-mercaptan was tracked (FIG. 7, Curve A); secondly, the coke formation rate on a freshly decoked sample during direct dosing of the n-heptane treated with 100 ppm tri-methyl-silyl-methyl-mercaptan was found FIG. 7, Curve B). FIG. 7 shows the results obtained. It is clear that the use according to the invention of compounds containing silicon and sulphur as an additive for continuous addition to the n-heptane used as the pyrolysis feed leads to a significant drop in the coke formation rate.

EXAMPLE 8

(Example According to the Invention)

In the same apparatus as described in Example 1, pre-activated samples of chrome-nickel-steel (X8CrNiTi18.10) were thermally pretreated with tri-methyl-silyl-methyl-mercaptan under the conditions stated in Example 5, and the coke formation rates on these samples during n-heptane pyrolysis, as in Examples 2 to 4, in dependence on additives containing different amounts of silicon and sulphur were then found.

The total amount of the additive compositions according to the invention that were added to the n-heptane was 120 ppm in each case. The coke formation rates measured in dependence on test time are summarized in Table 1. These rates indicate that, in place of compounds that simultaneously contain both silicon and sulphur, mixtures of silicon compounds and sulphur compounds also attain the same effect as coke formation inhibitors; the atomic ratio of silicon to sulphur can vary in the range between 1:1 and 5:1.

EXAMPLE 9

(Example According to the Invention)

In the same apparatus as described in Example 1, a sample of chrome-nickel-steel (X8CrNiTi18.10) was thermally pretreated with tri-methyl-silyl-methyl-mercaptan at 880° C., as in Example 5, and the coke formation rates on this sample during the pyrolysis of n-heptane treated with 100 ppm tri-methyl-silyl-methyl-mercaptan, in the presence of steam as the dilutent ($n_{heptane}:n_{H2O(D)}$=0.5) were then tracked. The results are summarized in Table 2. These results indicate that the additive compositions according to the invention are also effective in the presence of steam as the dilutent.

EXAMPLE 10 (Comparison and Invention)

In a laboratory pyrolysis apparatus as in Example 1, coke formation rates were investigated on five samples of chrome-nickel-steel (X8CrNiTi18.10) that had been thermally pretreated, as in Example 5, with tri-methyl-silyl-methyl-mercaptan at 880° C. in a equimolar mixture of hydrogen and methane for 60 minutes. The following were used as pyrolysis feeds (PEP):

PEP 1: pure n-heptane

PEP 2: 100 ppm tetra-methyl-silane in n-heptane

PEP 3: 100 ppm di-methyl-sulfide in n-heptane

PEP 4: 100 tri-methyl-silyl-methyl-mercaptan in n-heptane

PEP 5: 100 ppm of an equimolar mixture of tetra-methyl-silane and di-methyl-sulfide in n-heptane.

The pyrolysis temperature was 715° C.; the standing time was 1 s. The dilutent was nitrogen ($n_{heptane}:n_{N2}$=0.5). The coke formation rates found over a test time of 45 hours are summarized in Table 3.

Of the five pyrolysis feeds, only PEP 4 and PEP 5 are in accordance with the invention. A comparison shows that only when the samples composed according to the invention are used can the low coke formation rate be maintained over long test times.

TABLE 1

Dependence of coke formation rate r during pyrolysis of n-heptane in nitrogen flow (715° C., 1s) on the atomic ratio of silicon and sulphur in various additive compositions that were added to the n-heptane.

| | Atomic ratio of Si:S | | | | | |
|---|---|---|---|---|---|---|
| | a) | b) | c) | d) | e) | f) |
| | 1:1 | 1:1 | 2:1 | 2:1 | 3:1 | 5:1 |
| Test time [min] | r [$\mu$g · cm$^{-2}$ · min$^{-1}$] | | | | | |
| 10 | 4.5 | 4.5 | 6.0 | 5.7 | 7.4 | 20 |
| 30 | 5.0 | 5.1 | 5.2 | 5.0 | 7.6 | 19 |
| 50 | 4.8 | 4.7 | 5.8 | 6.1 | 7.5 | 21 |
| 70 | 5.1 | 4.6 | 5.8 | 6.0 | 7.8 | 18 |
| 90 | 4.5 | 4.5 | 6.1 | 6.2 | 7.6 | 22 |
| 100 | 4.9 | 4.8 | 6.2 | 6.0 | 7.7 | 22 |

The Si and S compounds used as additive components:

a) tri-methyl-silyl-methyl-mercaptan b) 1:1 mixture of tetra-methyl-silane and di-methyl-sulfide c) bis-tri-methyl-silyl-sulfide d) 2:1 mixture of tetra-methyl-silane and di-methyl-sulfide e) 3:1 mixture of tetra-methyl-silane and di-methyl-sulfide f) 5:1 mixture of tetra-methyl-silane and di-methyl-sulfide

TABLE 2

Dependence on test time of the influence that 100 ppm tri-methyl-silyl-methyl-mercaptan has on the coke formation rate r during the pyrolysis of n-heptane in the presence of steam (715° C., 1s).

| Test time [h] | r [g · cm$^{-2}$ · min$^{-1}$] |
|---|---|
| 0.5 | 4 |
| 1 | 3 |
| 2 | 5 |
| 5 | 4 |
| 8 | 4 |
| 12 | 7 |

TABLE 3

Dependence of the coke formation rate r on specially thermally pretreated samples of chrome-nickel-steel (X8CrNiTi18.10) on type of additives and test time.

| | Educt | | | | |
|---|---|---|---|---|---|
| Test time [h] | PEP 1 | PEP 2 | PEP 3 | PEP 4 | PEP 5 |
| | r [$\mu$g · cm$^{-2}$ · min$^{-1}$] | | | | |
| 1 | 60 | 58 | 3 | 5 | 3 |
| 3 | 58 | 57 | 3 | 4.5 | 5 |
| 5 | 57 | 56 | 4 | 4.5 | 4 |
| 10 | 55 | 54 | 12 | 5.5 | 7 |
| 20 | 52 | 51 | 17 | 7 | 7 |
| 30 | 51 | 56 | 28 | 6 | 9 |
| 40 | 47 | 49 | 27 | 9 | 8.5 |
| 50 | 49 | 49 | 36 | 8 | 10 |

We claim:

1. A process for producing thermally cracked products from hydrocarbons and simultaneously reducing coke deposits on a heat exchange surface, comprising the steps of:
adding to a feed product to be cracked 20 to 1000 ppm of an additive composition consisting of silicon, sulphur, carbon and hydrogen atoms wherein the silicon and sulphur atoms are in an atomic ratio of 5:1 to 1:1 and contacting the heat exchange surfaces with the additive composition at a temperature of 400° to 1000° C.

2. The process of claim 1, wherein the additive composition is a volatile organic compound and the feed product contains a sulphur component greater than 100 ppm which is volatile under cracking conditions.

3. The process of claim 2, wherein the heat exchange surface is a metal inner wall of a tubular reactor.

4. The process of claim 2, wherein the heat exchange surface is a metal inner wall of a heat exchanger.

5. The process of claim 2, wherein said composition comprises tri-methyl-silyl-mercaptan or its mixture with di-methyl-sulfide and/or tetra-methyl-silane.

6. The process of claim 2, wherein the feed product contains 50 to 400 ppm of the additive composition.

7. The process of claim 2, wherein the feed product contains 50 to 200 ppm of the additive composition.

8. The process of claim 2, wherein the cracked product is selected from the group consisting of alkenes, other lower olefines and diolefines.

9. The process of claim 2, wherein the cracked product is selected from the group consisting of ethylene, propylene, and butadiene.

10. The process of claim 2, wherein the temperature of the heat exchange surface is 800° to 1000° C.

11. The process of claim 3, wherein the temperature of the heat exchange surface is 700° to 1000° C.

12. The process of claim 4, wherein the temperature of the heat exchange surface is 400° to 750° C.

13. A process for producing thermally cracked products from hydrocarbons and simultaneously reducing coke deposits on a heat exchange surface, comprising the steps of:

adding to a feed product to be cracked 20 to 1000 ppm of an additive composition said additive composition comprising a silicon atom bonded to a sulphur atom and having an atomic ratio of silicon to sulphur of between 5:1 and 1:1; and contacting the heat exchange surface with the additive composition at a temperature of 400° to 1000° C.

* * * * *